United States Patent [19]

Barth

[11] 4,241,050
[45] Dec. 23, 1980

[54] PENAM 1,1-DIOXIDES AS BETA-LACTAMASE INHIBITORS

[75] Inventor: Wayne E. Barth, East Lyme, Conn.

[73] Assignee: Pfizer Inc., New York, N.Y.

[21] Appl. No.: 938,848

[22] Filed: Sep. 1, 1978

[51] Int. Cl.$^3$ ............... C07D 277/60; A61K 31/425; A61K 31/43
[52] U.S. Cl. .............................. 424/114; 260/245.2 R
[58] Field of Search ............... 260/239.1, 306.7 C, 260/245.2; 424/114

[56] References Cited

U.S. PATENT DOCUMENTS

| | | | |
|---|---|---|---|
| 3,197,466 | 7/1965 | Chow et al. | 260/239.1 |
| 3,536,698 | 10/1970 | Chauvette et al. | 260/239.1 |

FOREIGN PATENT DOCUMENTS 1072108  5/1964  United Kingdom ................. 260/239.1

OTHER PUBLICATIONS

Recent Advances in the Chemistry of β-Lactam Antibiotics, edited by J. Elks, Special Publication No. 28, pp. 304–313, Burlington House, (1977), London.

Guddaz et al., Tetrahedron Letters, No. 9, 381, (1962).

Harrison et al., Jour. Chem. Soc., (London), Perkin I, 1772, (1976).

Antibiotki, 13, 155–158, (1968).

Hoogmartens et al., Jour. of Med. Chem., 17, 389, (1974).

Claes et al., European Jour. of Med. Chem. Chimica Therapeutica, 10, 573, (1975).

Primary Examiner—Nicholas S. Rizzo
Attorney, Agent, or Firm—Connolly and Hutz

[57] ABSTRACT (3S, 5R)-Penam-3-carboxylic acid 1,1-dioxide, optionally having a methyl group at the 2-position, and esters thereof readily hydrolyzable in vivo, are useful for enhancing the effectiveness of several beta-lactam antibiotics against many beta-lactamase producing bacteria.

28 Claims, No Drawings

PENAM 1,1-DIOXIDES AS BETA-LACTAMASE INHIBITORS

BACKGROUND OF THE INVENTION

One of the most well-known and widely-used classes of antibacterial agents is the class known as the beta-lactam antibiotics. These compounds are characterized in that they have a nucleus consisting of a 2-azetidinone (beta-lactam) ring fused to either a thiazolidine or a dihydro-1,3-thiazine ring. When the nucleus contains a thiazolidine ring, the compounds are usually referred to generically as penicillins, whereas when the nucleus contains a dihydrothiazine ring, the compounds are referred to as cephalosporins. Typical examples of penicillins which are commonly used in clinical practice are benzylpenicillin (penicillin G), phenoxymethylpenicillin (penicillin V), ampicillin and carbenicillin; typical examples of common cephalosporins are cephalothin, cephalexin and cefazolin.

However, despite the wide use and wide acceptance of the beta-lactam antibiotics as valuable chemotherapeutic agents, they suffer from the major drawback that certain members are not active against certain microorganisms. It is thought that in many instances this resistance of a particular microorganism to a given beta-lactam antibiotic results because the microorganism produces a beta-lactamase. The latter substances are enzymes which cleave the betalactam ring of penicillins and cephalosporins to give products which are devoid of antibacterial activity. However, certain substances have the ability to inhibit beta-lactamases, and when a beta-lactamase inhibitor is used in combination with a penicillin or cephalosporin it can increase or enhance the antibacterial effectiveness of the penicillin or cephalosporin against certain microorganisms. It is considered that there is an enhancement of antibacterial effectiveness when the antibacterial activity of a combination of a beta-lactamase inhibiting substance and a beta-lactam antibiotic is significantly greater than the sum of the antibacterial activities of the individual components.

Thus, according to the invention, there are provided certain new chemical compounds which are potent inhibitors of microbial beta-lactamases. More specifically, these new chemical compounds are (3S,5R)-penam-3-carboxylic acid 1,1-dioxide, which optionally has a methyl group at the 2-position, and esters of these compounds which are readily hydrolyzable in vivo. Additionally, there is also provided a method for enhancing the effectiveness of beta-lactam antibiotics using said new chemical compounds. Yet further there are provided certain novel intermediates.

1,1-Dioxides of benzylpenicillin, phenoxymethylpenicillin and certain esters thereof have been disclosed in U.S. Pat. Nos. 3,197,466 and 3,536,698, and in an article by Guddal et al., in *Tetrahedron Letters*, No. 9, 381 (1962). Several penicillin derivatives were tested as potential beta-lactamase inhibitors by Chaikovskaya et al., *Antibiotiki*, 13, 155 (1968); benzylpenicillin 1,1-dioxide was found to be inactive. Harrison et al., in the *Journal of the Chemical Society* (London), Perkin I, 1772 (1976), have disclosed a variety of penicillin 1,1-dioxides, including methyl phthalimidopenicillinate 1,1-dioxide and methyl 6,6-dibromopenicillanate 1,1-dioxide. A penam derivative having no methyl groups at C-2 is disclosed by Hoogmattens et al., *Journal of Medicinal Chemistry*, 17, 389 (1974); and penam derivatives with one methyl group at C-2 are disclosed by Claes et al., *European Journal of Medicinal Chemistry, Chimica Therapeutica*, 10, 573 (1975). Penicillanic acid is known from British Pat. No. 1,072,108.

My copending application Ser. No. 890,451, filed March 29, 1978, discloses and claims compounds of the formula:

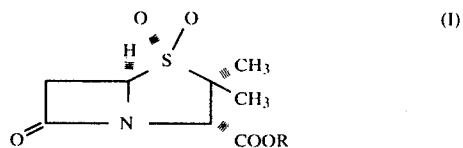

(I)

and the pharmaceutically-acceptable base salts thereof, wherein R is selected from the group consisting of hydrogen, ester-forming residues readily hydrolyzable in vivo, and conventional penicillin carboxy protecting groups. The compounds of the formula I, wherein R is hydrogen or an ester-forming residue readily hydrolyzable in vivo, are useful as antibacterial agents and for enhancing the antibacterial activity of beta-lactam antibiotics. Said compounds of the formula I, wherein R is a penicillin carboxy protecting group, are useful as chemical intermediates to the compound of the formula I, wherein R is hydrogen or an ester-forming residue readily hydrolyzable in vivo.

SUMMARY OF THE INVENTION

According to the invention there are provided novel compounds of the formula

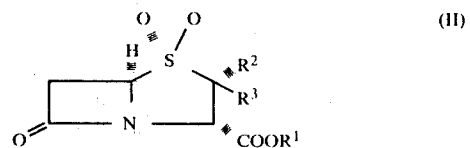

(II)

and the pharmaceutically-acceptable base salts thereof, wherein $R^1$ is selected from the group consistint of hydrogen, ester-forming residues readily hydrolyzable in vivo, and conventional penicillin carboxy protecting groups; and $R^2$ and $R^3$ are each selected from the group consisting of hydrogen and methyl; provided that $R^2$ and $R^3$ are not both methyl. The term "ester-forming residues readily hydrolyzable in vivo" is here intended to refer to non-toxic ester residues which are rapidly cleaved in mammalian blood or tissue, to release the corresponding free acid (i.e. the compound of formula II, wherein $R^1$ is hydrogen). Typical examples of such readily hydrolyzable ester-forming residues which can be used for $R^1$ are alkanoyloxymethyl having from 3 to 7 carbon atoms, 1-(alkanoyloxy)ethyl having from 4 to 8 carbon atoms, 1-methyl-1-(alkanoyloxy)ethyl having from 5 to 9 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, 3-phthalidyl, 4-crotonolactonyl and gamma-butyrolacton-4-yl.

Said compounds of the formula II, wherein $R^1$ is hydrogen or an ester-forming residue readily hydrolyzable in vivo, are useful for enhancing the antibacterial activity of beta-lactam antibiotics. Said compounds of the formula II, wherein $R^1$ is a penicillin carboxy protecting group, are useful as chemical intermediates to the compounds of the formula II, wherein $R^1$ is hydrogen or an ester-forming residue readily hydrolyzable in vivo. Typical carboxy protecting groups are benzyl and substituted benzyl, e.g. 4-nitrobenzyl.

Thus, the beta-lactamase inhibitors of the invention are the compounds of the formula

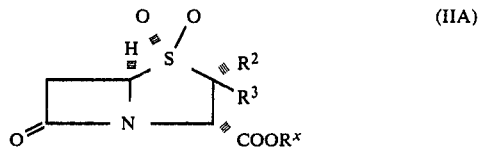

and the pharmaceutically-acceptable base salts thereof, wherein $R^x$ is selected from the group consisting of hydrogen and ester-forming residues readily hydrolyzable in vivo; $R^2$ and $R^3$ are each selected from the group consisting of hydrogen and methyl; provided that $R^2$ and $R^3$ are not both methyl.

DETAILED DESCRIPTION OF THE INVENTION

In this specification certain compounds are named as derivatives of "penam" and "2-azetidinone". These names are intended to refer to ring systems III and IV, respectively.

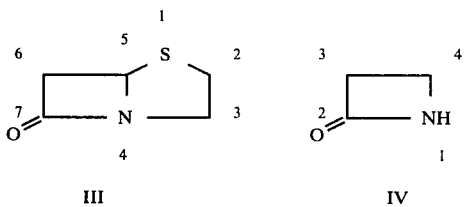

In derivatives of compounds of formulas III and IV, broken line attachment of a substituent to the ring system indicates that the substituent is below the plane of the ring system and such a substituent is said to be in the alpha-configuration. Conversely, solid line attachment of a substituent to the ring system indicates that the substituent is attached above the plane of the ring system, and this latter configuration is referred to as the beta-configuration. Wavy line attachment of a substituent to the ring system denotes a mixture of epimers at the position of attachment. In side-chains attached to the 2-azetidinone, stereochemistries are denoted using the R and S method (Cahn and Ingold, J. Chem. Soc., London, 612 (1951); Cahn, Ingold and Prelog, Experientia, 12, 81 [1956]).

As indicated hereinbefore, the compounds of this invention are the compounds of formula II, and the pharmaceutically-acceptable base salts thereof. When $R^1$ is an ester-forming residue readily hydrolyzable in vivo in a compound of formula II, it is a grouping which is notionally derived from an alcohol of the formula $R^1$—OH, such that the moiety COOR$^1$ in such a compound of formula II represents an ester grouping. Moreover, $R^1$ is of such a nature that the grouping COOR$^1$ is readily cleaved in in vivo to liberate a free carboxy group (COOH). That is to say, $R^1$ is a group of the type that when a compound of formula II, wherein $R^1$ is an ester-forming residue readily hydrolyzed in vivo, is exposed to mammalian blood or tissue, the compound of formula II, wherein $R^1$ is hydrogen, is readily produced. Such groups for $R^1$ are well-known in the penicillin art. In most instances they improve the absorption characteristics of the penicillin compound. Additionally, $R^1$ should be of such a nature that it imparts pharmaceutically-acceptable properties to a compound of formula II, and it liberates pharmaceutically-acceptable fragments when cleaved in vivo.

As indicated above, ester-forming residues readily hydrolyzable in vivo are well-known and are readily identified by those skilled in the penicillin art. See, for example, West German Offenlegungsschrift No. 2,517,316. Typical examples of such groups for $R^1$ are 3-phthalidyl, 4-crotonolactonyl, gamma-butyrolacton-4-yl and groups of the formula

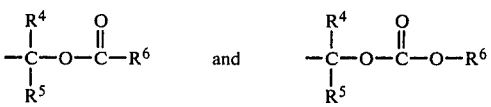

wherein $R^4$ and $R^5$ are each selected from the group consisting of hydrogen and alkyl having from 1 to 2 carbon atoms, and $R^6$ is alkyl having from 1 to 6 carbon atoms. However, preferred groups for $R^1$ are alkanoyloxymethyl having from 3 to 7 carbon atoms, 1-(alkanoyloxy)ethyl having from 4 to 8 carbon atoms, 1-methyl-1-(alkanoyloxy)ethyl having from 5 to 9 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, 3-phthalidyl, 4-crotonolactonyl and gamma-butyrolacton-4-yl.

The manner in which the compounds of formula II, wherein $R^1$, $R^2$ and $R^3$ are as defined previously, can be prepared can be seen by reference to the Scheme. In the first step, 4-acetoxy-2-azetidinone (VII) is reacted with a protected amino-acid of the formula VIII, wherein $R^2$ and $R^3$ are as defined previously and $R^7$ is a carboxy protecting group. The reaction is usually carried out by contacting approximately equimolar proportions of the two reactants in an appropriate solvent, such as aqueous tetrahydrofuran or an aqueous lower-alkanol, at a pH of from about 8 to about 10. The reaction is normally conducted at about 0° C., and normally it is substantially complete in a few hours, e.g. 2 hours. The product of formula IX can be recovered by the standard procedure of solvent extraction.

The compound of formula IX is then converted into the diazo compound X, wherein $R^2$, $R^3$ and $R^7$ are as defined previously. This is a diazotization reaction, and a variety of conventional diazotizing reagents can be used; however, a convenient reagent is amyl nitrite. In a typical procedure the compound of formula IX is treated with one molar equivalent of amyl nitrite and about one third of a molar equivalent of an organic carboxylic acid such as acetic acid. The reaction is normally run in an inert organic solvent such as chloroform, and at a temperature of about 50° to 100° C. The reaction usually takes about one half to about one hour. At the end of the reaction, the reaction mixture is diluted with water and the product is recovered by extraction into a water-immiscible organic solvent.

SCHEME

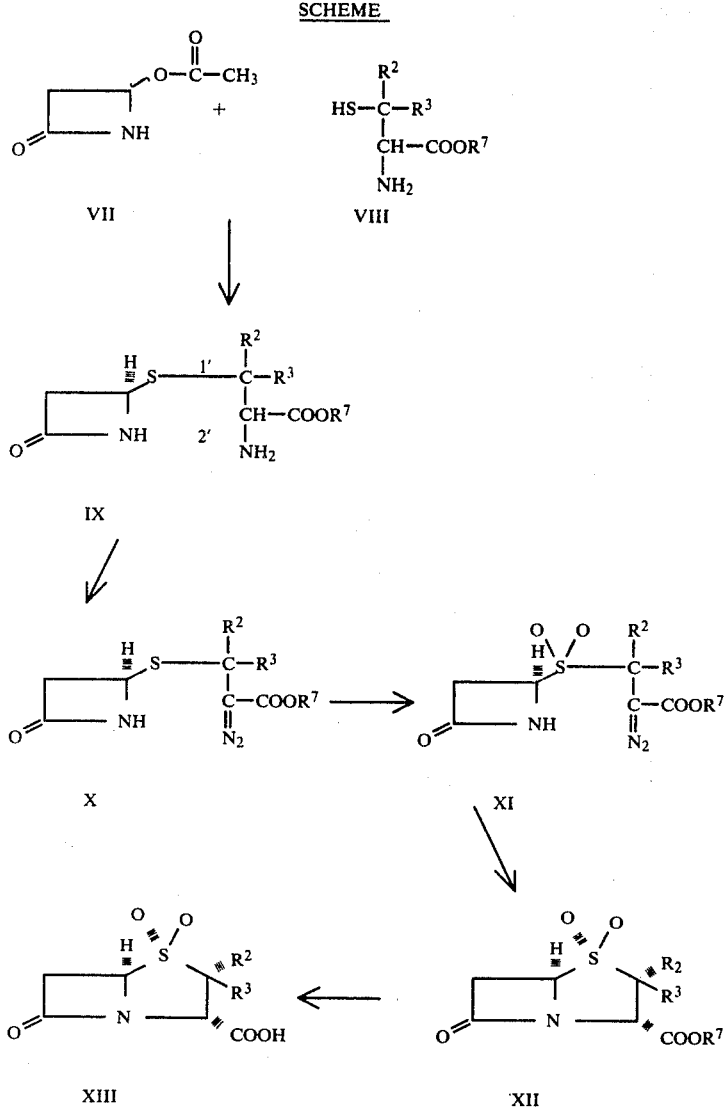

The compound of formula X is then oxidized to the sulfone (XI), wherein $R^2$, $R^3$ and $R^7$ are as defined previously. A wide variety of agents known in the art for oxidizing sulfides to sulfones can be used, and particularly convenient reagents are organic peroxycarboxylic acid, e.g. 3-chloroperbenzoic acid. When a compound of the formula X is oxidized to the corresponding compound of the formula XI, using a peroxycarboxylic acid, the reaction is usually carried out by treating the compound of the formula X with from about 1.8 to about 6 molar equivalents, and preferably about 2.2 molar equivalents, of the oxidant in a reaction-inert organic solvent. Typical solvents are chlorinated hydrocarbons, such as dichloromethane, chloroform and 1,2-dichloroethane; and ethers, such as diethyl ether, tetrahydrofuran and 1,2-dimethoxyethane. The reaction is normally carried out at a temperature of from about −20° to about 50° C., and preferably at about 25° C. At about 25° C. reaction times of about 2 to about 16 hours are commonly used. The product is normally isolated by removal of the solvent by evaporation in vacuo. The product can be purified by conventional methods, well-known in the art.

In the next step of the Scheme, the diazo compound XI is decomposed and ring closure takes place to give the penam compound of formula XII, wherein $R^2$, $R^3$ and $R^7$ are as defined previously. A convenient way of carrying out this transformation comprises treating a solution of a compound of the formula XI, in a reaction-inert solvent, with a catalytic amount of a rhodium catalyst. By the term "reaction-inert solvent" is meant a solvent which will substantially dissolve the compound of formula XI, and which will not adversely affect either the compound of formula XI or the compound of formula XII. Typical solvents include hydrocarbons such as benzene and toluene; ethers such as diethyl ether, tetrahydrofuran and 1,2-dimethoxyethane; low molecular weight esters such as ethyl acetate and butyl acetate; chlorinated hydrocarbons such as dichloromethene and chloroform; and acetonitrile. Appropriate rhodium catalysts are rhodium(II) dicarboxylates having from two to seven carbon atoms in each carboxylate residue. A preferred catalyst is rhodium(II) diacetate. From about 0.1 to about 1 mole-percent of the catalyst is normally used, but larger amounts can be used if desired. The reaction is usually carried out at a temperature of from about 0° to about 50° C., and preferably at about 25° C. At about 25° C., the reaction typically takes about 1 hour. The product can be isolated by standard techniques, e.g. removal of the solvent by evaporation in vacuo, and the proudct so obtained can be purified by standard methods, e.g. recrystallization or chromatography.

In the final step of the Scheme, the carboxy protecting group $R^7$ is removed to liberate a free carboxy group. The manner in which this is carried out depends on the nature of the particular protecting group chosen. In general, a variety of protecting groups conventionally used in the penicillin art to protect the 3-carboxy group can be employed. The identity of the protecting group is not critical. The only requirements for the protecting group are that: (i) it must be stable during the individual steps of the Scheme; and (ii) it must be removable from the compound of formula XII, using conditions under which the beta-lactam ring system remains substantially intact. For these reasons, typical examples are the benzyl group, substituted benzyl groups (e.g. 4-nitrobenzyl), the benzhydryl group, the 2,2,2-trichloroethyl group, the t-butyl group and the phenacyl group. See further U.S. Pat. Nos. 3,632,850 and 3,197,466; British Pat. No. 1,041,985, Woodward et al., Journal of the American Chemical Society, 88, 852 (1966); Chauvette, Journal of Organic Chemistry, 36, 1259 (1971); Sheehan et al., Journal of Organic Chemistry, 29, 2006 (1964); and "Cephalosporin and Penicillins, Chemistry and Biology", edited by H. E. Flynn, academic Press, Inc., 1972. The penicillin carboxy protecting group is removed in conventional manner, having due regard for the lability of the beta-lactam ring system. Conditions which are compatible with the beta-lactam ring system are well-known to those skilled in the art.

Particularly useful protecting groups for $R^7$ are the benzyl group, substituted benzyl groups and the benzhydryl group, and especially benzyl. These groups can be removed conveniently by catalytic hydrogenolysis. In this case, a solution of said compound of the formula XII, wherein $R^7$ is benzyl, substituted benzyl or benzhydryl, is stirred or shaken under an atmosphere of hydrogen, or hydrogen mixed with an inert diluent such as nitrogen or argon, in the presence of a catalytic amount of palladium-on-carbon catalyst. Convenient solvents for this hydrogenolysis are lower-alkanols, such as methanol; ethers, such as tetrahydrofuran and dioxan; low molecular weight esters, such as ethyl acetate and butyl acetate; water; and mixtures of these solvents. However, it is usual to choose conditions under which the starting material is soluble. The hydrogenolysis is usually carried out at room temperature and at a pressure from about 0.5 to about 5 kg/cm². The catalyst is usually present in an amount from about 10 percent by weight based on the starting material up to an amount equal in weight to the starting material, although larger amounts can be used. The reaction commonly takes about one hour, after which the compound of the formula II, wherein $R^1$ is hydrogen, is recovered simply by filtration followed by removal of the solvent in vacuo.

A further particularly useful protecting group $R^7$ is the 2,2,2-trichloroethyl group. This group can be removed by treating the compound of the formula XII, wherein $R^7$ is 2,2,2-trichloroethyl, with zinc dust in acetic acid, formic acid or a phosphate buffer, according to well-known methods. See further: Woodward et al., Journal of the American Chemical Society, 88, 852 (1966); Pike et al., Journal of Organic Chemistry, 34, 3552 (1969); Just et al., Synthesis, 457 (1976).

The compounds of the formula II, wherein $R^1$ is hydrogen and $R^2$ and $R^3$ are as defined previously, can be purified, if desired, by methods well-known in the art, e.g. recrystallization or chromatography.

Compounds of the formula II, wherein $R^1$ is an ester-forming residue readily hydrolyzable in vivo, and $R^2$ and $R^3$ are as defined previously, can be prepared directly from the corresponding compound of formula II, wherein $R^1$ is hydrogen, by esterification. The specific method chosen will depend naturally upon the precise structure of the ester-forming residue, but an appropriate method will be readily selected by one skilled in the art. In the case wherein $R^1$ is selected from the group consisting of 3-phthalidyl, 4-crotonolactonyl, gamma-butyrolacton-4-yl and groups of the formula V and VI, wherein $R^4$, $R^5$ and $R^6$ are as defined previously, they can be prepared by alkylation of the appropriate compound of formula II, wherein $R^1$ is hydrogen, with a 3-phthalidyl halide, a 4-crotonolactonyl halide, a gamma-butyrolacton-4-yl halide or a compound of the formula

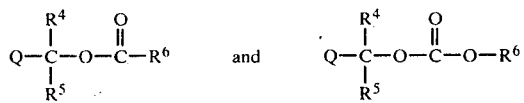

wherein Q is halo, and $R^4$, $R^5$ and $R^6$ are as previously defined. The terms "halide" and "halo" are intended to mean derivatives of chlorine, bromine and iodine. The reaction is conveniently carried out by dissolving a salt of said compound of formula II, wherein $R^1$ is hydrogen, in a suitable, polar, organic solvent, such as N,N-dimethylformamide, and then adding about one molar equivalent of the halide. When the reaction has proceeded essentially to completion, the product is isolated by standard techniques. It is often sufficient simply to dilute the reaction medium with an excess of water, and then extract the product into a water-immiscible organic solvent and then recover same by solent evaporation. Salts of the starting material which are commonly used are alkali metal salts, such as sodium and potassium salt, and tertiary amine salts, such as triethylamine, ethyldiisopropylamine, N-ethylpiperidine, N,N-dimethylaniline and N-methylmorpholine salts. The reaction is run at a temperature in the range from about 0° to 100° C., and usually at about 25° C. The length of time needed to reach completion varies according to a variety of factors, such as the concentration of the reactants and the reactivity of the reagents. Thus, when considering the halo compound, the iodide reacts faster than the bromide, which in turn reacts faster than the chloride. In fact, it is sometimes advantageous, when utilizing a chloro compound, to add up to one molar equivalent of an alkali metal iodide. This has the effect of speeding up the reaction. With full regard for the foregoing factors, reaction times of from about 1 to about 24 hours are commonly used.

The compounds of formula II, wherein $R^1$ is hydrogen, and $R^2$ and $R^3$ are as previously defined, are acidic and will form salts with basic agents. These salts can be prepared by standard techniques, such as contacting the acidic and basic components, usually in a stoichiometric ratio, in an aqueous, non-aqueous or partially aqueous medium, as appropriate. They are then recovered by filtration, by precipitation with a non-solvent followed by filtration, by evaporation of the solvent, or in the case of aqueous solutions, by lyophilization, as appropriate. Basic agents which are suitably employed in salt formation belong to both the organic and inorganic types, and they include ammonia, organic amines, alkali metal hydroxides, carbonates, bicarbonates, hydrides and alkoxides, as well as alkaline earth metal hydroxides, carbonates, hydrides and alkoxides. Representative examples of such bases are primary amines, such as n-propylamine, n-butylamine, aniline, cyclohexylamine, benzylamine and octylamine; secondary amines, such as diethylamine, morpholine, pyrrolidine and piperidine; tertiary amines, such as triethylamine, N-ethylpiperidine, N-methylmorpholine and 1,5-diazabicyclo[4.3.0]-non-5-ene; hydroxides, such as sodium hydroxide, potassium hydroxide, ammonium hydroxide and barium hydroxide; alkoxides, such as sodium ethoxide and potassium ethoxide; hydrides, such as calcium hydride and sodium hydride; carbonates, such as potassium carbonate and sodium carbonate; bicarbonates, such as sodium bicarbonate, and potassium bicarbonate; and alkali metal salts of long-chain fatty acids, such as sodium 2-ethylhexanoate.

As indicated previously, the compounds of this invention are the compounds of the formula II, and they have the S-configuration at the 3-position and the R-configuration at the 5-position. When carrying out the sequence of reactions depicted in the Scheme, it is usual to use the racemic form of the azetidinone of formula VII as the starting material. Under these circumstances it is advantageous to use a single isomer of the compound of formula VIII. In the case wherein $R^2$ and $R^3$ are both hydrogen, it is advantageous to use either L-cysteine (2R-cysteine) or D-cysteine (2S-cysteine) in pure form for VIII. In like manner, when $R^2$ or $R^3$ is methyl, it is advantageous to use a compound of formula VIII which is a single isomer at the 2-and 3-positions. By proceeding in this manner, the product obtained by reacting VII with VIII is a pair of diastereoisomers, which differ from each other only in their configuration at the 4-position of the azetidinone ring. These diastereoisomers can be separated by conventional crystallization or chromatography, and either of the diastereoisomers, or a mixture thereof, can be used for completion of the steps of the Scheme.

When the compound of formula IX is converted into the compound of formula X, no changes in stereochemistry occur at the 4-position of the azetidinone ring or at the 1'-position of the side chain. However, the 2'-position of the side chain loses its chirality. When the compound of the formula X is converted into the compound of formula XI, no change in stereochemistry occurs.

When the compound of formula XI is cyclized to the compound of formula XII, the ring closure takes place in a stereoselective manner. The ring closure takes place such that in the compound of formula XII the hydrogen atom at the ring junction (C-5) bears a cis relationship to the protected carboxy group at C-3. When the compound of formula XII is deprotected, this takes place without change in stereochemistry. Similarly, esterification of the compound of formula II, wherein $R^1$ is is hydrogen, takes place without change in stereochemistry.

As a result of the foregoing, if one carries out the sequence IX to X to XI to XII starting with the compound of formula IX as a mixture of diastereoisomers, one obtains XII as a mixture of two compounds. One compound has the 3S,5R-configuration; the other compound has the 3R,5S configuration. If one uses the compound of formula IX having the R configuration at C-4 of the azetidinone ring, one obtains the compound XII as a pure isomer having the 3S, 5R configuration. By the same token, the compound of formula IX having C-4 of the azetidinone ring in the S configuration leads to the compound of formula XII having the 3R,5S configuration.

When contemplating therapeutic use of a compound of this invention as a beta-lactamase inhibitor, the active compounds which have the 3S,5R configuration, and mixtures containing these compounds are also active. The compounds having the 3S,5R configuration can be distinguished from the 3R,5S enantiomers by measuring their optical rotations at the D line of sodium. The compounds having 3S,5R stereochemistry rotate the plane of plane-polarized light to the right (i.e. they are dextrorotatory); the compounds having 3R,5S stereochemistry rotate the plane of plane-polarized light to the left (they are levorotatory).

4-Acetoxy-2-azetidinone is prepared by the method of Clauss et al., *Liebigs Annalen der Chemie*, 539 (1974). L-Cysteine benzyl ester hydrochloride is prepared from L-cysteine by the method of Zervas and Photaki, *Journal of the American Chemical Society*, 84, 3892 (1962). D-Cysteine benzyl ester hydrochloride is prepared similarly from D-cysteine. The 2S,3R, 2S,3S, 2R,3S and 2R,3R isomers of 2-amino-3-mercaptobutyric acid are prepared by the method of Hoogmartens et al., *Journal of Organic Chemistry*, 39, 425 (1974).

As indicated hereinbefore, the compounds of the formula IIA, are inhibitors of microbial beta-lactamases, and they increase the antibacterial effectiveness of beta-lactam antibiotics (penicillins and cephalosporins) against many microorganisms which produce a beta-lactamase. The manner in which the compounds of the formula IIA, wherein $R^x$ is hydrogen, increase the effectiveness of a beta-lactam antibiotic in vitro can be appreciated by reference to experiments in which the MIC (Minimum Inhibitory Concentration) of a given antibiotic alone, and said compound of the formula IIA alone, are measured. These MIC's are then compared with the MIC values obtained with a combination of the given antibiotic and the compound of the formula IIA. When the antibacterial potency of the combination is significantly greater than would have been predicted from the potencies of the individual compounds, this is considered to constitute enhancement of activity. The MIC values of combinations are measured using the method described by Barry and Sabath in "Manual of Clinical Microbiology", edited by Lenette, Spaulding and Truant, 2nd edition, 1974, American Society for Microbiology.

The compounds of the formula IIA, and salts thereof, enhance the antibacterial effectiveness of beta-lactam antibiotics in vivo, and they lower the amount of antibiotic which is needed to protect mice against an otherwise lethal inoculum of certain beta-lactamase producing bacteria.

The ability of the compounds of the formula IIA, and salts thereof, to enhance the effectiveness of a beta-lactam antibiotic against beta-lactamase-producing bacteria makes them valuable for co-administration with beta-lactam antibiotics in the treatment of bacterial infections in mammals, particularly man. In the treatment of a bacterial infection, said compound of the formula IIA can be comingled with the beta-lactam antibiotic, and the two agents thereby administered simultaneously. Alternatively, said compound of the formula IIA can be administered as a separate agent during a course of treatment with a beta-lactam antibiotic. In some instances it will be advantageous to predose the subject with the compound of the formula IIA before initiating treatment with a beta-lactam antibiotic.

When using a compound of formula IIA, or a salt thereof to enhance the effectiveness of a beta-lactam antibiotic, it can be administered alone, or it can be mixed with pharmaceutically acceptable carriers or diluents. It can be administered orally or parenterally, i.e. intramuscularly, subcutaneously or intraperitoneally. The carrier or diluent is chosen on the basis of the intended mode of administration. For example, when considering the oral mode of administration, a compound of this invention of formula IIA can be used in the form of tablets, capsules, lozenges, troches, powders, syrups, elixirs, aqueous solutions and suspensions, and the like, in accordance with standard pharmaceutical practice. In the case of tablets for oral use, carriers which are commonly used include lactose, sodium citrate and salts of phosphoric acid. Various disintegrants such as starch, and lubricating agents, such as magnesium stearate, sodium lauryl sulfate and talc, are commonly used in tablets. For oral administration in capsule form, useful diluents are lactose and high molecular weight polyethylene glycols. When aqueous suspensions are required for oral use, the active ingredient is combined with emulsifying and suspending agents. If desired, certain sweetening and/or flavoring agents can be added. For parenteral administration, which includes intramuscular, intraperitoneal, subcutaneous and intravenous use, sterile solutions of the active ingredient are usually prepared, and the pH of the solutions are suitably adjusted and buffered. For intravenous use, the total concentration of solutes should be controlled to render the preparation isotonic. A pharmaceutical composition containing a compound of this invention will normally contain from about 5 to about 80 percent of the pharmaceutically acceptable carrier by weight.

When using a compound of this invention in combination with another beta-lactam antibiotic, the compound can be administered orally or parenterally, i.e. intramuscularly, subcutaneously or intraperitoneally. Although the prescribing physician will ultimately decide the dosage to be used in a human subject, the ratio of the daily dosages of the penam of this invention and the beta-lactam antibiotic will normally be in the range from about 1:3 to 3:1. Additionally, when using a compound of this invention in combination with another beta-lactam antibiotic, the daily oral dosage of each component will normally be in the range from about 10 to about 200 mg per kilogram of body weight and the daily parenteral dosage of each component will normally be about 10 to about 400 mg per kilogram of body weight. These figures are illustrative only, however, and in some cases it may be necessary to use dosages outside these limits.

Typical beta-lactam antibiotics with which a compound of formula IIA or salts or esters readily hydrolyzable in vivo can be co-administered are:
6-(2-phenylacetamido)penicillanic acid,
6-(2-phenoxyacetamido)penicillanic acid,
6-(2-phenylpropionamido)penicillanic acid,
6-(D-2-amino-2-phenylacetamido)penicillanic acid,
6-(D-2-amino-2-[4-hydroxyphenyl]acetamido)penicillanic acid,
6-(D-2-amino-2-[1,4-cyclohexadienyl]acetamido)penicillanic acid,
6-(1-aminocyclohexanecarboxamido)penicillanic acid,
6-(2-carboxy-2-phenylacetamido)penicillanic acid,
6-(2-carboxy-2-[3-thienyl]acetamido)penicillanic acid,
6-(D-2-[4-ethylpiperazin-2,3-dione-1-carboxamido]-2-phenylacetamido)penicillanic acid,
6-(D-2-[4-hydroxy-1,5-naphthyridine-3-carboxamido]-2-phenylacetamido)penicillanic acid,
6-(D-2-sulfo-2-phenylacetamido)penicillanic acid,
6-(D-2-sulfoamino-2-phenylacetamido)penicillanic acid,
6-(D-2-[imidazolidin-2-one-1-carboxamido]-2-phenylacetamido)penicillanic acid,
6-(D-[3-methylsulfonylimidazolidin-2-one-1-carboxamido]-2-phenylacetamido)penicillanic acid,
6-([hexahydro-1H-azepin-1-yl]methyleneamino)penicillanic acid,
acetoxymethyl 6-(2-phenylacetamido)penicillanate,
acetoxymethyl 6-(D-2-amino-2-phenylacetamido)penicillanate,
acetoxymethyl 6-(D-2-amino-2-[4-hydroxyphenyl]acetamido)penicillanate,
pivaloyloxymethyl 6-(2-phenylacetamido)penicillanate,
pivaloyloxymethyl 6-(D-2-amino-2-phenylacetamido)penicillanate,
pivaloyloxymethyl 6-(D-2-amino-2-[4-hydroxyphenyl]acetamido)penicillanate,
1-(ethoxycarbonyloxy)ethyl 6-(2-phenylacetamido)penicillanate,
1-(ethoxycarbonyloxy)ethyl 6-(D-2-amino-2-phenylacetamido)penicillanate,
1-(ethoxycarbonyloxy)ethyl 6-(D-2-amino-2-[4-hydroxyphenyl]acetamido)penicillanate,
3-phthalidyl 6-(2-phenylacetamido)penicillanate,
3-phthalidyl 6-(D-2-amino-2-phenylacetamido)penicillanate,
3-phthalidyl 6-(D-2-amino-2-[4-hydroxyphenyl]acetamido)penicillanate,
6-(2-phenoxycarbonyl-2-phenylacetamido)penicillanic acid,
6-(2-tolyloxycarbonyl-2-phenylacetamido)penicillanic acid,
6-(2-[5-indanyloxycarbonyl]-2-phenylacetamido)penicillanic acid,
6-(2-phenoxycarbonyl-2-[3-thienyl]acetamido)penicillanic acid,
6-(2-tolyloxycarbonyl-2-[3-thienyl]acetamido)penicillanic acid,
6-(2-[5-indanyloxycarbonyl]-2-[3-thienyl]acetamido)penicillanic acid,
6-(2,2-dimethyl-5-oxo-4-phenyl-1-imidazolidinyl)penicillanic acid,
7-(2-[2-thienyl]acetamido)cephalosporanic acid,
7-(2-[1-tetrazolyl]acetamido-3-(2-[5-methyl-1,3,4-thiadiazolyl]thiomethyl)-3-desacetoxymethylcephalosporanic acid,
7-(D-2-amino-2-phenylacetamido)desacetoxycephalosporanic acid,
7-alpha-methoxy-7-(2-[2-thienyl]acetamido)-3-carbamoyloxymethyl-3-desacetoxymethylcephalosporanic acid,
7-(2-cyanoacetamido)cephalosporanic acid,
7-(D-2-hydroxy-2-phenylacetamido)-3-(5-[1-methyltetrazolyl]thiomethyl)-3-desacetoxymethylcephalosporanic acid, 7-(2-[4-pyridylthio]acetamido)cephalosporanic acid,
7-(D-2-amino-2-[1,4-cyclohexadienyl]acetamido)cephalosporanic acid,
7-(D-2-amino-2-phenylacetamido)cephalosporanic acid, and
the pharmaceutically-acceptable salts thereof.

As will be appreciated by one skilled in the art, some of the above beta-lactam compounds are effective when administered orally or parenterally, while others are effective only when administered by the parenteral route. When a compound of formula IIA, or a salt or an ester thereof readily hydrolyzable in vivo, is to be used simultaneously (i.e. co-mingled) with a beta-lactam antibiotic which is effective only on parenteral administration, a combination formulation suitable for parenteral use will be required. When the compound of formula IIA or salt or ester thereof is to be used simultaneously (co-mingled) with a beta-lactam antibiotic which is effective orally or parenterally, combinations suitable for either oral or parenteral administration can be prepared. Additionally, it is possible to administer preparations of the compound of formula IIA or salt or ester thereof orally, while at the same time administering a further beta-lactam antibiotic parenterally; and it is also possible to administer preparations of the compound of formula IIA or salt or ester thereof parenterally, while at the same time administering the further beta-lactam antibiotic orally.

The following examples are provided solely for the purpose of further illustration. Infrared (IR) spectra were measured as potassium bromide discs (KBr discs) or as liquid films, and diagnostic absorption bands are reported in wave numbers (cm$^{-1}$). Nuclear magnetic resonance spectra (NMR) were measured at 60 or 100 MHz for solutions in deuterochloroform (CDCl$_3$), per-deuterio dimethyl sulfoxide (DMSO-d$_6$) or deuterium oxide (D$_2$O), and peak positions are expressed in parts per million (ppm) downfield from tetramethylsilane or sodium 2,2-dimethyl-2-silapentane-5-sulfonate. The following abbreviations for peak shapes are used: s, singlet; d, doublet; t, triplet; q, quartet; m, multiplet.

EXAMPLE 1

Benzyl (3S, 5R and 3R, 5S)-Penam-3-carboxylate 1,1-Dioxide

To 1.5 mg of dirhodium tetracetate in 60 ml of 1,2-dimethoxyethane, under nitrogen, at room temperature, was added, dropwise, during 30 minutes, a solution of 660 mg of (4RS)-4-(2'-diazo-2'-benzyloxycarbonylethylsulfonyl)-2-azetidinone in 15 ml of 1,2-dimethoxyethane. The mixture was stirred for 1.75 hours and then an additional 2 mg of dirhodium tetraacetate was added. Stirring was continued for an additional 1.5 hours and then the 1,2-dimethoxyethane was removed by evaporation in vacuo. The residue was dissolved in ethyl acetate and the solution was washed with water. The solution was dried (Na$_2$SO$_4$) and the ethyl acetate was removed by evaporation in vacuo. The residue was stored at ca. 5° C. for three days, during which time it solidified, affording 360 mg of the title compound. The NMR spectrum (60 MHz; CDCl$_3$) showed absorptions at 7.25 (s, 5H), 5.12 (s, 2H), 4.72 (t, 1H), 4.37 (m, 1H), 3.48 (m, 2H) and 3.32 (m, 2H) ppm. The IR spectrum showed absorptions at 1785 and 1740 cm$^{-1}$. The mass spectrum showed a parent ion at m/e=295 and other prominent ions at m/e's of 231, 189 and 91.

EXAMPLE 2

Cyclization of (4RS, 1'R)-4-(2'-diazo-2'-benzyloxycarbonyl-1'-methylethylsulfonyl)-2-azetidinone and (4RS, 1'S)-4-(2'-diazo-2'-benzyloxycarbonyl-1'-methylethylsulfonyl)-2-azetidinone, respectively, with dirhodium tetraacetate, according to the procedure of Example 1, affords:

benzyl (2R, 3S, 5R and 2R, 3R, 5S)-2-methylpenam-3-carboxylate 1,1-dioxide and
benzyl (2S, 3S, 5R and 2S, 3R, 5S)-2-methylpenam-3-carboxylate 1,1-dioxide, respectively.

EXAMPLE 3

(3S, 5R and 3R, 5S)-Penam-3-carboxylic Acid 1,1-Dioxide

To a solution of 350 mg of benzyl (3S, 5R and 3R, 5S)penam-3-carboxylate 1,1-dioxide in 12 ml of methanol was added 75 mg of potassium bicarbonate followed by 350 mg of 10% palladium on carbon. The mixture was shaken under an atmosphere of hydrogen at atmospheric pressure until hydrogen absorption ceased. The catalyst was removed by filtration and then the solvent was removed by evaporation in vacuo. The residue was partitioned between water and ethyl acetate at pH 8. The aqueous layer was removed, and the pH was lowered to 1.5. The acidic aqueous phase was extracted liberally with ethyl acetate. The ethyl acetate extracts were combined, dried (Na$_2$SO$_4$) and concentrated in vacuo. The residue was recrystallized from ethyl acetate-methanol, to give 41 mg of the title compound, mp 164°–167° C. The NMR spectrum (100 MHz; DMSO-d$_6$) showed absorptions at 4.97 (m, 1H), 4.86 (q, 1H), 3.90 (m, 2H) and 3.65 (m, 2H) ppm. The IR spectrum (film) showed absorptions at 1770 and 1725 cm$^{-1}$. The product had no optical activity.

EXAMPLE 4

Hydrogenoloysis of benzyl (2R, 3S, 5R and 2R, 3R, 5S)-2-methylpenam-3-carboxylate 1,1-dioxide and benzyl (2S, 3S, 5R and 2S, 3R, 5S)-2-methylpenam-3-carboxylate 1,1-dioxide, respectively, according to the procedure of Example 3, affords:

(2R, 3S, 5R and 2R, 3R, 5S)-2-methylpenam-3-carboxylic acid 1,1-dioxide and
(2S, 3S, 5R and 2S, 3R, 5S)-2-methylpenam-3-carboxylic acid 1,1-dioxide, respectively.

EXAMPLE 5

Benzyl (3S, 5R)-Penam-3-Carboxylate 1,1-Dioxide

To a stirred solution of 1.80 g of (4R)-4-(2'-diazo-2'-benzyloxycarbonylethylsulfonyl)-2-azetidinone in 100 ml of 1,2-dimethoxyethane was added 3 mg of dirhodium tetraacetate. The reaction mixture was stirred for 1.5 hours and then a further 3 mg of dirhodium tetraacetate was added. Stirring was continued for 2.5 hours, and then the solvent was removed by evaporation in vacuo. The residue was dissolved in ethyl acetate, and the solution was washed twice with water at pH 8.5. The ethyl acetate solution was dried (Na$_2$SO$_4$) and evaporated in vacuo to give 0.88 g of product. This crude product was chromatographed on 26 g of silica gel and the product containing fractions were combined and evaporated. The residue was dissolved in boiling chloroform and then hexane was added to induce precipitation. The precipitate was recovered by filtration giving 131 mg of the title compound. The NMR spectrum (60 MHz; CDCl₃) showed absorptions at 7.22 (s, 5H), 5.10 (s, 2H), 4.70 (m, 1H), 4.35 (m, 1H), 3.47 (m, 2H) and 3.32 (m, 2H) ppm. The IR spectrum (film) showed absorptions at 1800 and 1735 cm$^{-1}$.

EXAMPLE 6

(3S, 5R)-Penam-3-Carboxylic Acid 1,1-Dioxide

To a solution of 131 mg of benzyl (3S, 5R)-penam-3-carboxylate 1,1-dioxide in a mixture of 15 ml of methanol and 10 ml of ethyl acetate was added 100 mg of 10% palladium on carbon. The mixture was stirred under an atmosphere of hydrogen at atmospheric pressure until hydrogen uptake ceased. At this point, the reaction mixture was filtered and the solvent was removed by evaporation in vacuo. This afforded 106 mg of the title compound [alpha]$_D^{25}$=203 (CH₃OH; C=1). The NMR spectrum (60 MHz; D₂O) showed absorptions at 4.85 (m, 1H), 4.82 (m, 1H), 3.85 (m, 2H) and 3.43 (m, 2H) ppm. The IR spectrum (film) showed absorptions at 1760 and 1730 cm$^{-1}$.

EXAMPLE 7

Pivaloyloxymethyl (3S, 5R)-penam-3-carboxylate 1,1-Dioxide

To a stirred solution of 2.05 g of (3S, 5R)-penam-3-carboxylic acid 1,1-dioxide in 10 ml of N,N-dimethylformamide is added 1.30 g of diisopropylethylamine followed by 1.50 g of chloromethyl pivalate and 50 mg of sodium iodide at ca. 0° C. The reaction mixture is stirred at ca. 0° C. for 30 minutes and then at room temperature for 24 hours. The reaction mixture is then diluted with ethyl acetate and water and the pH of the aqueous phase is adjusted to 7.5. The ethyl acetate layer is separated and washed three times with water and once with saturated sodium chloride solution. The ethyl acetate solution is then dried using anhydrous sodium sulfate, and evaporated in vacuo to give the title compound.

EXAMPLE 8

Reaction of the appropriate penam-3-carboxylic acid 1,1-dioxide with 3-phthalidyl chloride, 4-crotonolactonyl chloride, gamma-butyrolacton-4-yl chloride or the requisite alkanoyloxymethyl chloride, 1-(alkanyloxy)ethyl chloride, 1-methyl-1-(alkanoyloxy)ethyl chloride, alkoxycarbonyloxymethyl chloride, 1-(alkoxycarbonyloxy)ethyl chloride or 1-methyl-1-(alkoxycarbonyloxy)ethyl chloride, according to the procedure of Example 7, affords the following compounds:
3-phthalidyl (3S, 5R and 3R, 5S)-penam-3-carboxylate 1,1-dioxide,
4-crotonolactonyl (2R, 3S, 5R and 2R, 3R, 5S)-2-methylpenam-3-carboxylate 1,1-dioxide,
gamma-butyrolacton-4-yl (2S, 3S, 5R and 2S, 3R, 5S)-2-methylpenam-3-carboxylate 1,1-dioxide,
acetoxymethyl (3S, 5R and 3R, 5S)-penam-3-carboxylate 1,1-dioxide,
pivaloyloxymethyl (2R, 3S, 5R and 2R, 3R, 5S)-2-methylpenam-3-carboxylate 1,1-dioxide,
hexanoyloxymethyl (2S, 3S, 5R and 2S, 3R, 5S)-2-methylpenam-3-carboxylate 1,1-dioxide,
1-(acetoxy)ethyl (3S, 5R and 3R, 5S)-penam-3-carboxylate 1,1-dioxide,
1-(isobutyryloxy)ethyl (2R, 3S, 5R and 2R, 3R, 5S)-2-methylpenam-3-carboxylate 1,1-dioxide,
1-methyl-1-(acetoxy)ethyl (2S, 3S, 5R and 2S, 3R, 5S)-2-methylpenam-3-carboxylate 1,1-dioxide,
1-methyl-1-(hexanoyloxy)ethyl (3S, 5R and 3R, 5S)-penam-3-carboxylate 1,1-dioxide,
methoxycarbonyloxymethyl (2R, 3S, 5R and 2R, 3R, 5S)-2-methylpenam-3-carboxylate 1,1-dioxide,
propoxycarbonyloxymethyl (2S, 3S, 5R and 2S, 3R, 5S)-2-methylpenam-3-carboxylate 1,1-dioxide,
1-(ethoxycarbonyloxy)ethyl (3S, 5R and 3R, 5S)-penam-3-carboxylate 1,1-dioxide,
1-(butoxycarbonyloxy)ethyl (2R, 3S, 5R and 2R, 3R, 5S)-2-methylpenam-3-carboxylate 1,1-dioxide,
1-methyl-1-(methoxycarbonyloxy)ethyl (2S, 3S, 5R and 2S, 3R, 5S)-2-methylpenam-3-carboxylate 1,1-dioxide and
1-methyl-1-(isopropoxycarbonyloxy)ethyl (2R, 3S, 5R and 2R, 3R, 5S)-2-methylpenam-3-carboxylate 1,1-dioxide, respectively.

PREPARATION 1

(4RS, 2′R)-4-(2′-Amino-2′-benzyloxycarbonylethylthio)-2-azetidinone

To a stirred solution of 16.9 g of the benzyl ester hydrochloride of L-cysteine in 90 ml of tetrahydrofuran was added 40 ml of water and the mixture was cooled to ice temperature. The pH was adjusted to 4.5 and a solution of 8.75 g of (4RS)-4-acetoxy-2-azetidinone in 50 ml of tetrahydrofuran was added. The reaction system was flushed with nitrogen and the pH was raised to 9.0 to 9.5. Stirring was continued until all the azetidinone had reacted (ca. 2 hours). At this point, 100 ml of ethyl acetate was added and the layers were separated. The organic layer was washed with water and with brine, and then it was dried using sodium sulfate. Removal of the solvent afforded 15.5 g (71% yield) of the title compound as a yellow oil. This crude product was purified by chromatography on silica gel using methanol/chloroform mixtures as eluant.

PREPARATION 2

Reaction of (4RS)-4-acetoxy-2-azetidinone with (2S, 3R)-2-amino-3-mercaptobutyric acid and (2S, 3S)-2-amino-3-mercaptobutyric acid, respectively, according to the procedure of Preparation 1, affords:
(4RS, 1′R, 2′S)-4-(2′-amino-2′-benzyloxycarbonyl-1′-methylethylthio)-2-azetidinone and
(4RS, 1′S, 2′S)-4-(2′-amino-2′-benzyloxycarbonyl-1′-methylethylthio)-2-azetidinone, respectively.

PREPARATION 3

(4RS)-4-(2′-Diazo-2′-benzyloxycarbonylethylthio)-2-azetidinone

To a stirred solution of 6.83 g of (4RS, 2′R)-4-(2′-amino-2′-benzyloxycarbonylethylthio)-2-azetidinone in 200 ml of chloroform was added 0.416 ml of glacial acetic acid followed by 3.913 ml of amyl nitrite. The reaction mixture was heated under reflux for 0.5 hour. It was then cooled to 25° C. and diluted with an equal volume of water. The pH was adjusted to 2.5. The layers were separated and the chloroform layer was washed with water and dilute sodium bicarbonate, and then it was dried. The solvent was removed by evaporation in vacuo leaving 5.6 g of product. The IR spectrum (film) showed absorptions at 2090, 1750 and 1690 cm$^{-1}$.

PREPARATION 4

Diazotization of (4RS, 1′R, 2′S)-4-(2′-amino-2′-benzyloxycarbonyl-1′-methylethylthio)-2-azetidinone and (4RS, 1'S, 2'S)-4-(2'-amino-2'-benzyloxycarbonyl-1'-methylethylthio)-2-azetidinone, respectively, according to the procedure of Preparation 4 affords:

(4RS, 1'R)-4-(2'-diazo-2'-benzyloxycarbonyl-1'-methylethylthio)-2-azetidinone and (4RS, 1'S)-4-(2'-diazo-2'-benzyloxycarbonyl-1'-methylethylthio)-2-azetidinone, respectively.

PREPARATION 5

(4RS)-4-(2'-Diazo-2'-benzyloxycarbonylethylsulfonyl)-2-azetidinone

A stirred solution of 4.03 g of (4RS)-4-(2'-diazo-2'-benzyloxycarbonylethylthio)-2-azetidinone in 70 ml of ethyl acetate was cooled to −10° C. and 111 ml of phosphate buffer (pH=6.7) were added. At −10° C., 2.23 g of 3-chloroperbenzoic acid was added, followed a few minutes later by a further 2.23 g portion of 3-chloroperbenzoic acid. The reaction mixture was stirred for 25 minutes and then the layers were separated. The ethyl acetate layer was washed three times with ice-cold phosphate buffer (pH 6.7) and then it was dried ($Na_2SO_4$). The solvent was removed by evaporation in vacuo and chloroform was added to the residue. The insoluble material was filtered off and discarded, and the chloroform solution was evaporated in vacuo. The residue was chromatographed on silica gel, eluting with chloroformethyl acetate mixture, to give 660 mg (15% yield) of the title product. The NMR spectrum (60 MHz; $CDCl_3$) showed absorptions at 7.43 (s, 5H), 5.32 (s, 2H), 4.68 (q, 1H), 4.02 (q, 2H) and 3.37 (m, 2H) ppm.

PREPARATION 6

Oxidation of (4RS, 1'R)-4-(2'-diazo-2'-benzyloxycarbonyl-1'-methylethylthio)-2-azetidinone and (4RS, 1'S)-4-(2'-diazo-2'-benzyloxycarbonyl-1'-methylethylthio)-2-azetidinone with 3-chloroperbenzoic acid, according to the procedure of Preparation 5, affords:

(4RS, 1'R)-4-(2'-diazo-2'-benzyloxycarbonyl-1'-methylethylsulfonyl)-2-azetidinone and (4RS, 1'S)-4-(2'-diazo-2'-benzyloxycarbonyl-1'-methylethylsulfonyl)-2-azetidinone, respectively.

PREPARATION 7

(4R, 2'R)-4-(2'-Amino-2'-benzyloxycarbonylethylthio)-2-azetidinone 4-Toluenesulfonate To a stirred solution of 7.86 g of (4RS, 2'R)-4-(2'-amino-2'-benzyloxycarbonylethylthio)-2-azetidinone in 15 ml of ethyl acetate was added, dropwise, a concentrated solution of 2.47 g of 4-toluenesulfonic acid monohydrate in ethyl acetate. The mixture became cloudy and a small crystal of the title compound (obtained from an earlier experiment) was added as a seed. (The use of seed is not necessary, it merely hastens the crystallization process). Stirring was continued for 20 minutes and then the precipitate was recovered by filtration. It was washed with ethyl acetate to give 3.05 g of the title compound as a crystalline solid, $[alpha]_D^{25} = 29.6°$ (95:5 chloroform/DMSO, C=0.1). The NMR spectrum (60 MHz; $CDCl_3$) showed absorptions at 7.43 (q, 4H), 7.40 (s, 5H), 5.25 (s, 2H), 4.78 (m, 1H), 4.35 (m, 1H), 3.28 (m, 4H) and 2.37 (s, 3H).

PREPARATION 8

(4R)-4-(2'-Diazo-2'-benzyloxycarbonylethylthio)-2-azetidinone (4R, 2'R)-4-(2'-Amino-2'-benzyloxycarbonylethylthio)-2-azetidinone 4-toluenesulfonate (2.34 g) was partitioned between 25 ml of ethyl acetate and 25 ml of water at pH 9.0. The ethyl acetate layer was removed, washed with water and dried. Removal of the solvent by evaporation in vacuo, followed by two recrystallizations of the residue afforded 2.34 g of (4R, 2'R)-4-(2'-amino-2'-benzyloxycarbonylethylthio)-2-azetidinone free base.

The 2.34 g of free base was dissolved in 50 ml of chloroform, and 1.456 ml of amyl nitrite and 0.262 g of 3-chlorobenzoic acid were added. The reaction mixture was heated under reflux under nitrogen for 20 minutes and then it was cooled to room temperature. The solvent was removed by evaporation in vacuo, and the residue was chromatographed on 90 g of alumina using chloroformethyl acetate as eluant. This afforded 1.07 g of the title compound.

PREPARATION 9

(4R)-4-(2'-Diazo-2'-benzyloxycarbonylethylsulfonyl)-2-azetidinone

A stirred solution of 1.07 g of (4R)-4-(2'-diazo-2'-benzyloxycarbonylethylthio)-2-azetidinone in 15 ml of dichloromethane was cooled to −15° C. under nitrogen and 1.63 g of 85% pure 3-chloroperbenzoic acid was added. The reaction mixture was stirred at −15° C. until the starting material had disappeared, and then it was filtered. The filtrate was maintained at 0° C., and ice-cold water was added. The pH was adjusted to 7.5 and the layers were separated. The organic layer was washed with ice-cold water, dried ($Na_2SO_4$) and evaporated in vacuo at ca. 0° C. This afforded 0.93 g of the title compound.

What is claimed is:

1. A compound of the formula

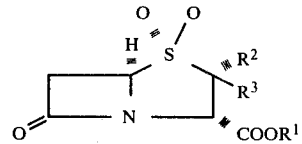

and the pharmaceutically acceptable base salts thereof, wherein $R^1$ is selected from the group consisting of hydrogen, alkanoyloxymethyl having from 3 to 7 carbon atoms, 1-(alkanoyloxy)ethyl having from 4 to 8 carbon atoms, 1-methyl-1-(alkanoyloxy)ethyl having from 5 to 9 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, 3-phthalidyl, 4-crotonolactonyl and gamma-butyrolacton-4-yl, benzyl, 4-nitrobenzyl, benzhydryl, 2,2,2-trichloroethyl, t-butyl and phenacyl;

and $R^2$ and $R^3$ are each selected from the group consisting of hydrogen and methyl;

provided that $R^2$ and $R^3$ are not both methyl.

2. A compound according to claim 1, wherein $R^2$ and $R^3$ are each hydrogen.

3. The compound according to claim 2, wherein $R^1$ is hydrogen.

4. A compound according to claim 1, wherein $R^1$ is said alkanoyloxymethyl.

5. The compound according to claim 4, wherein $R^1$ is pivaloyloxymethyl.

6. The compound according to claim 1, wherein $R^1$ is 1-(ethoxycarbonyloxy)ethyl.

7. A compound according to claim 2, wherein $R^1$ is benzyl, 4-nitrobenzyl, benzhydryl, 2,2,2-trichloroethyl, t-butyl or phenacyl.

8. The compound according to claim 7, wherein $R^1$ is benzyl.

9. A compound according to claim 1, wherein $R^2$ is hydrogen and $R^3$ is methyl.

10. The compound according to claim 9, wherein $R^1$ is hydrogen.

11. A compound according to claim 1, wherein $R^2$ is methyl and $R^3$ is hydrogen.

12. The compound according to claim 11, wherein $R^1$ is hydrogen.

13. A pharmaceutical composition useful for treating bacterial infections in mammals which comprises (A) a β-lactam antibiotic and (B) the compound of the formula

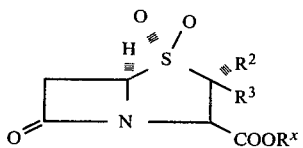

or a pharmaceutically acceptable base salt thereof, the weight ratio of (A) to (B) being 1:3 to 3:1, $R^x$ being selected from the group consisting of hydrogen, alkanoyloxymethyl having from 3 to 7 carbon atoms, 1-(alkanoyloxy)ethyl having from 4 to 8 carbon atoms, 1-methyl-1-(alkanoyloxy)ethyl having from 5 to 9 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, 3-phthalidyl, 4-crotonolactonyl and gamma-butyrolacton-4-yl; $R^2$ and $R^3$ each being selected from the group consisting of hydrogen or methyl providing that $R^2$ and $R^3$ are not both methyl and said β-lactam antibiotic being selected from the group consisting of
6-(2-phenylacetamido)penicillanic acid,
6-(2-phenoxyacetamido)penicillanic acid,
6-(2-phenylpropionamido)penicillanic acid,
6-(D-2-amino-2-phenylacetamido)penicillanic acid,
6-(D-2-amino-2-[4-hydroxyphenyl]acetamido)penicillanic acid,
6-(D-2-amino-2-[1,4-cyclohexadienyl]acetamido)penicillanic acid,
6-(1-aminocyclohexanecarboxamido)penicillanic acid,
6-(2-carboxy-2-phenylacetamido)penicillanic acid,
6-(2-carboxy-2-[3-thienyl]acetamido)penicillanic acid,
6-(D-2-[4-ethylpiperazin-2,3-dione-1-carboxamido]-2-phenylacetamido)penicillanic acid,
6-(D-2-[4-hydroxy-1,5-naphthyridine-3-carboxamido]-2-phenylacetamido)penicillanic acid,
6-(D-2-sulfo-2-phenylacetamido)penicillanic acid,
6-(D-2-sulfoamino-2-phenylacetamido)penicillanic acid,
6-(D-2-[imidazolidin-2-one-1-carboxamido]-2-phenylacetamido)penicillanic acid,
6-(D-[3-methylsulfoylimidazolidin-2-one-1-carboxamido]2-phenylacetamido)penicillanic acid,
6-(hexahydro-1H-azepin-1-yl]methyleneamino)penicillanic acid,
acetoxymethyl 6-(2-phenylacetamido)penicillanate,
acetoxymethyl 6-(D-2-amino-2-phenylacetamido)penicillanate,
acetoxymethyl 6-(D-2-amino-2-[4-hydroxyphenyl]acetamido)penicillanate,
pivaloyloxymethyl 6-(2-phenylacetamido)penicillanate,
pivaloyloxymethyl 6-(D-2-amino-2-phenylacetamido)penicillanate,
pivaloyloxymethyl 6-(D-2-amino-2-[4-hydroxyphenyl]acetamido)penicillanate,
1-(ethoxycarbonyloxy)ethyl 6-(2-phenylacetamido)penicillanate,
1-8ethoxycarbonyloxy)ethyl 6-(D-2-amino-2-phenylacetamido)penicillanate,
1-(ethoxycarbonyloxy)ethyl 6-(D-2-amino-2-[4-hydroxyphenyl]acetamido)penicillanate,
3-phthalidyl 6-(2-phenylacetamido)penicillanate,
3-phthalidyl 6-(D-2-amino-2-phenylacetamido)penicillanate,
3-phthalidyl 6-(D-2-amino-2-[4-hydroxyphenyl]acetamido)penicillanate,
6-(2-phenoxycarbonyl-2-phenylacetamido)penicillanic acid,
6-(2-tolyloxycarbonyl-2-phenylacetamido)penicillanic acid,
6-(2-[5-indanyloxycarbonyl]-2-phenylacetamido)penicillanic acid,
6-(2-phenoxycarbonyl-2-[3-thienyl]acetamido]penicillanic acid,
6-(2-tolyloxycarbonyl-2-[3-thienyl]acetamido)penicillanic acid,
6-(2-[5-indanyloxycarbonyl]-2-[3-thienyl]acetamido)penicillanic acid,
6-(2,2-dimethyl-5-oxo-4-phenyl-1-imidazolidinyl)penicillanic acid,
7-(2-[2-thienyl]acetamido)caphalosporanic acid,
7-(2-[1-tetrazolyl]acetamido-3-(2-[5-methyl-1,3,4-thiadiazolyl]thiomethyl)-3-desacetoxymethylcephalosporanic acid,
7-(D-2-amino-2-phenylacetamido)desacetoxycephalosporanic acid,
7-alpha-methoxy-7-(2-[2-thienyl]acetamido)-3-carbamoyloxymethyl-3-desacetoxymethylcephalosporanic acid,
7-(2-cyanoacetamido)cephalosporanic acid,
7-(D-2-hydroxy-2-phenylacetamido)-3-(5-[1-methyltetrazolyl]thiomethyl)-3-desacetoxymethylcephalosporanic acid,
7-(2-[4-pyridylthio]acetamido)cephalosporanic acid,
7-(D-2-amino-2-[1,4-cyclohexadienyl]acetamido)cephalosporanic acid,
7-(D-2-amino-2-phenylacetamido)cephalosporanic acid, and the pharmaceutically-acceptable salts thereof.

14. A pharmaceutical composition according to claim 13, wherein $R^x$ is hydrogen.

15. A pharmaceutical composition according to claim 13, wherein $R^x$ is 1-(ethoxycarbonyloxy)ethyl.

16. A pharmaceutical composition according to claim 13, wherein $R^x$ is pivaloyloxymethyl.

17. A pharmaceutical composition according to claim 13, wherein said beta-lactam antibiotic is selected from the group consisting of 6-(2-phenylacetamido)penicillanic acid and the pharmaceutically-acceptable salts thereof.

18. A pharmaceutical composition according to claim 13, wherein said beta-lactam antibiotic is selected from the group consisting of 6-(2-phenoxyacetamido)penicillanic acid and the pharmaceutically-acceptable salts thereof.

19. A pharmaceutical composition according to claim 13, wherein said beta-lactam antibiotic is selected from the group consisting of 6-(D-2-amino-2-phenylacetamido)penicillanic acid and the pharmaceutically-acceptable salts thereof.

20. A pharmaceutical composition according to claim 13, wherein said beta-lactam antibiotic is selected from the group consisting of 1-(ethoxycarbonyloxy)ethyl 6-(D-2-amino-2-phenylacetamido)penicillanate and the pharmaceutically-acceptable salts thereof.

21. A method of treating a bacterial infection in a mammal subject which comprises administering to said subject (A) a β-lactam antibiotic and (B) a compound of the formula

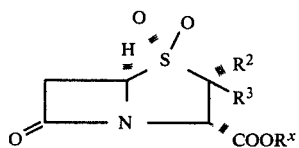

or a pharmaceutically-acceptable base salt thereof, the weight ratio of (A) to (B) administered being in the range of 1:3 to 3:1; the combined amounts of (A) and (B) administered constituting an antibacterially effective dosage; $R^x$ being selected from the group consisting of hydrogen, alkanoyloxymethyl having from 3 to 7 carbon atoms, 1-(alkanoyloxy)-ethyl having from 4 to 8 carbon atoms, 1-methyl-1-(alkanoyloxy)-ethyl having from 5 to 9 carbon atoms, alkoxycarbonyloxymethyl having from 3 to 6 carbon atoms, 1-(alkoxycarbonyloxy)ethyl having from 4 to 7 carbon atoms, and 1-methyl-1-(alkoxycarbonyloxy)ethyl having from 5 to 8 carbon atoms, 3-phthalidyl, 4-crotonolactonyl and gamma-butyrolacton-4-yl;

$R^2$ and $R^3$ being each selected from the group consisting of hydrogen and methyl provided the $R^2$ and $R^3$ are not both methyl and said β-lactam antibiotic being selected from the group consisting of 6-(2-phenylacetamido)penicillanic acid,
6-(2-phenoxyacetamido)penicillanic acid,
6-(2-phenylpropionamido)penicillanic acid,
6-(D-2-amino-2-phenylacetamido)penicillanic acid,
6-(D-2-amino-2-[4-hydroxyphenyl]acetamido)penicillanic acid,
6-(D-2-amino-2-[1,4-cyclohexadienyl]acetamido)penicillanic acid,
6-(1-aminocyclohexanecarboxamido)penicillanic acid,
6-(2-carboxy-2-phenylacetamido)penicillanic acid,
6-(2-carboxy-2-[3-thienyl]acetamido)penicillanic acid,
6-(D-2-[4-ethylpiperazin-2,3-dione-1-carboxamido]-2-phenylacetamido)penicillanic acid,
6-(D-2-[4-hydroxy-1,5-naphthyridine-3-carboxamido]-2-phenylacetamido)penicillanic acid,
6-(D-2-sulfo-2-phenylacetamido)penicillanic acid,
6-(D-2-sulfoamino-2-phenylacetamido)penicillanic acid,
6-(D-2-[imidazolidin-2-one-1-carboxamido]-2-phenylacetamido)penicillanic acid,
6-(D-[3-methylsulfonylimidazolidin-2-one-1-carboxamido]2-phenylacetamido)penicillanic acid,
6-([hexahydro-1H-azepin-1-yl]methyleneamino)penicillanic acid,
acetoxymethyl 6-(2-phenylacetamido)penicillanate,
acetoxymethyl 6-(D-2-amino-2-phenylacetamido)penicillanate,
acetoxymethyl 6-(D-2-amino-2-[4-hydroxyphenyl]acetamido)penicillanate,
pivaloyloxymethyl 6-(2-phenylacetamido)penicillanate,
pivaloyloxymethyl 6-(D-2-amino-2-phenylacetamido)penicillanate,
pivaloyloxymethyl 6-(D-2-amino-2-[4-hydroxyphenyl]acetamido)penicillanate,
1-(ethoxycarbonyloxy)ethyl 6-(2-phenylacetamido)penicillanate,
1-(ethoxycarbonyloxy)ethyl 6-(D-2-amino-2-phenylacetamido)penicillanate,
1-(ethoxycarbonyloxy)ethyl 6-(D-2-amino-2-[4-hydroxyphenyl]acetamido)penicillanate,
3-phthalidyl 6-(2-phenylacetamido)penicillanate,
3-phthalidyl 6-(D-2-amino-2-phenylacetamido)penicillanate,
3-phthalidyl 6-(D-2-amino-2-[4-hydroxyphenyl]acetamido)penicillanate,
6-(2-phenoxycarbonyl-2-phenylacetamido)penicillanic acid,
6-(2-tolyloxycarbonyl-2-phenylacetamido)penicillanic acid,
6-(2-[5-indanyloxycarbonyl]-2-phenylacetamido)penicillanic acid,
6-(2-phenoxycarbonyl-2-[3-thienyl]acetamido)penicillanic acid,
6-(2-tolyloxycarbonyl-2-[3-thienyl]acetamido)penicillanic acid,
6-(2-[5-indanyloxycarbonyl]-2-[3-thienyl]acetamido)penicillanic acid,
6-(2,2-dimethyl-5-oxo-4-phenyl-1-imidazolidinyl)penicillanic acid,
7-(2-[2-thienyl]acetamido)cephalosporanic acid,
7-(2-[1-tetrazolyl]acetamido-3-(2-[5-methyl-1,3,4-thiadiazolyl]thiomethyl)-3-desacetoxymethylcephalosporanic acid,
7-(D-2-amino-2-phenylacetamido)desacetoxycephalosporanic acid,
7-alpha-methoxy-7-(2-[2-thienyl]acetamido)-3-carbamoyloxymethyl-3-desacetoxymethylcephalosporanic acid,
7-(2-cyanoacetamido)cephalosporanic acid,
7-(D-2-hydroxy-2-phenylacetamido)-3-(5-[1-methyltetrazolyl]thiomethyl)-3-desacetoxymethylcephalosporanic acid,
7-(2-[4-pyridylthio]acetamido)cephalosporanic acid,
7-(D-2-amino-2-[1,4-cyclohexadienyl]acetamido)cephalosporanic acid,
7-(D-2-amino-2-phenylacetamido)cephalosporanic acid, and
the pharmaceutically-acceptable salts thereof.

22. The method according to claim 21, wherein $R^x$ is hydrogen.

23. The method according to claim 21, wherein $R^x$ is 1-(ethoxycarbonyloxy)ethyl.

24. The method according to claim 21, wherein $R^x$ is pivaloyloxymethyl.

25. The method according to claim 21, wherein said beta-lactam antibiotic is selected from the group consisting of 6-(2-phenylacetamido)penicillanic acid and the pharmaceutically-acceptable salts thereof.

26. The method according to claim 21, wherein said beta-lactam antibiotic is selected from the group consisting of 6-(2-phenoxyacetamido)penicillanic acid and the pharmaceutically-acceptable salts thereof.

27. The method according to claim 21, wherein said beta-lactam antibiotic is selected from the group consisting of 6-(D-2-amino-2-phenylacetamido)penicillanic acid and the pharmaceutically-acceptable salts thereof.

28. The method according to claim 21, wherein said beta-lactam antibiotic is selected from the group consisting of 1-(ethoxycarbonyloxy)ethyl 6-(D-2-amino-2-phenylacetamido)penicillanate and the pharmaceutically-acceptable salts thereof.

* * * * *

UNITED STATES PATENT AND TRADEMARK OFFICE
CERTIFICATE OF CORRECTION

PATENT NO. : 4,241,050
DATED : December 23, 1980
INVENTOR(S) : Wayne E. Barth

It is certified that error appears in the above-identified patent and that said Letters Patent are hereby corrected as shown below:

On the title page, between [73] and [21], should read
--[*] Notice: The portion of the term of this patent subsequent to November 18, 1997, has been disclaimed.--

On the title page, the second entry under "OTHER PUBLICATIONS," "Guddaz" should read --Guddal--.

On the title page, the fourth entry under "OTHER PUBLICATIONS," "Antibiotki" should read --Antibiotiki--.

Column 20, line 15, "1-8ethoxycarbonyloxy)ethyl" should read -- 1-(ethoxycarbonyloxy)ethyl.--

Signed and Sealed this

Fourteenth Day of April 1981

[SEAL]

Attest:

RENE D. TEGTMEYER

Attesting Officer    Acting Commissioner of Patents and Trademarks